United States Patent
Barth et al.

(10) Patent No.: US 11,124,574 B2
(45) Date of Patent: Sep. 21, 2021

(54) SPECIFIC PHOTOIMMUNO-THERANOSTICS FOR DETECTION AND ELIMINATION OF SKIN CANCER CELLS

(71) Applicant: University of Cape Town, Rondebsch (ZA)

(72) Inventors: Stefan Barth, Cape Town (ZA); Ahmad Fawzi Hussain, Aachen (DE); Rainer Fischer, Indianapolis, IN (US)

(73) Assignee: UNIVERSITY OF CAPE TOWN, Rondebsch (ZA)

( * ) Notice: Subject to any disclaimer, the term of this patent is extended or adjusted under 35 U.S.C. 154(b) by 258 days.

(21) Appl. No.: 15/736,271

(22) PCT Filed: Jun. 16, 2015

(86) PCT No.: PCT/EP2015/063422
§ 371 (c)(1),
(2) Date: Dec. 13, 2017

(87) PCT Pub. No.: WO2016/202365
PCT Pub. Date: Dec. 22, 2016

(65) Prior Publication Data
US 2019/0071506 A1    Mar. 7, 2019

(51) Int. Cl.
| | |
|---|---|
| C07K 16/28 | (2006.01) |
| A61K 41/00 | (2020.01) |
| A61K 47/64 | (2017.01) |
| A61K 47/68 | (2017.01) |
| A61P 35/00 | (2006.01) |
| C12N 15/62 | (2006.01) |

(52) U.S. Cl.
CPC ...... *C07K 16/2863* (2013.01); *A61K 41/0061* (2013.01); *A61K 41/0071* (2013.01); *A61K 47/64* (2017.08); *A61K 47/6849* (2017.08); *A61P 35/00* (2018.01); *C12N 15/62* (2013.01)

(58) Field of Classification Search
None
See application file for complete search history.

(56) References Cited

FOREIGN PATENT DOCUMENTS

| | | | |
|---|---|---|---|
| WO | 2013/139391 A1 | | 9/2013 |
| WO | 2013139391 | * | 9/2013 |

OTHER PUBLICATIONS

Hussain, Dissertation, Sep. 28, 2012 [retrieved from the internet] https://pdfs.semanticscholar.org/e88e/C5bd79d7dc16e5e17b8bfd1032211b58561d.pdf?_ga=2.237 [retrieved on Jan. 22, 2020] (Year: 2012).*
Cole, CurrProtoc Protein Sci.; 2014, 73: 30.1.1-30.1.16. doi:10.1002/0471140864.ps3001s73 (Year: 2014).*

(Continued)

*Primary Examiner* — Karl J Puttlitz
(74) *Attorney, Agent, or Firm* — Wagenknecht IP Law Group PC

(57) ABSTRACT

The technology provided herein generally relates to novel specific photoimmuno-theranostics for the use in detection and elimination of skin cancer cells. The technology also relates to novel methods which generate homogeneous and specific photoimmuno-theranostics reagents in a simple, controlled and efficient way. This method combines molecular optical imaging, photodynamic therapy and immunotherapy using SNAP-tag technology.

5 Claims, 8 Drawing Sheets

Specification includes a Sequence Listing.

(56) References Cited

OTHER PUBLICATIONS

Kishimoto et al., Free Radical Biology and Medicine 85 (2015) 24-3226 (Year: 2015).*
Hussain, Ahmad Fawzi. "Specific delivery of therapeutic agents against cancers." Von der Fakultaet fuer Mathematik, Informatik and Naturwissenschaften der RWTH Aachen University zur Erlangung des akademischen Grades eines Doktors der Naturwissenschaften genehmigte Dissertation, Sep. 28, 2012 [retrieved from the Internet] http://publications.rwth-aachen.de-record/197541/files/4326.pdf [retrieved on Feb. 10, 2016], 103 pages.
Hussain et al. "Targeted Delivery of Dendritic Polyglycerol-Doxorubicin Conjugates by scFv-SNAP Fusion Protein Suppresses EGFR+ Cancer Cell Growth," BioMacromolecules, Jun. 19, 2013, 14(8)1510-2520.
Hussain et al. "SNAP-Tag Technology Mediates Site Specific Conjugation of Antibody Fragments with a Photosensitizer and Improves Target Specific Phototoxicity in Tumor Cells," BioConjugate Chemistry, Oct. 13, 2011, 22(12)2487-2495.
PCT/EP2015/063422 International Search Report and Written Opinion dated Feb. 18, 2015.
"IRDye 700DX NHS Ester," LI-COR, 1-4 [Retrieved from the Internet: URL: https://www.licor.com/bio/reagents/rdye-700dx-nhs-ester [retrieved on Oct. 5, 2020]].

\* cited by examiner

FIGURE 8

SEQ ID No. 1: scFv-425 amino acid sequence
MAQVQLQQSGAELVKPGASVKLSCKASGYTFTSHWMHWVKQRAGQGLEWIGEFNPSNGRTN
YNEKFKSKATLTVDKSSSTAYMQLSSLTSEDSAVYYCASRDYDYDGRYFDYWGQGTTVTVSSG
GGGSGGGGSGGGGSDIELTQSPAIMSASPGEKVTMTCSASSSVTYMYWYQQKPGSSPRLLIYDT
SNLASGVPVRFSGSGSGTSYSLTISRMEAEDAATYYCQQWSSHIFTFGSGTELEIKR SEQ ID No. 2: SNAP-tag amino acid sequence
MDKDCEMKRTTLDSPLGKLELSGCEQGLHEIKLLGKGTSAADAVEVPAPAAVLGGPEPLMQAT
AWLNAYFHQPEAIEEFPVPALHHPVFQQESFTRQVLWKLLKVVKFGEVISYQQLAALAGNPAA
TAAVKTALSGNPVPILIPCHRVVSSSGAVGGYEGGLAVKEWLLAHEGHRLGKP SEQ ID No. 3: scFv-425-SNAP-tag amino acid sequence MAQVQLQQSGAELVKPGASVKLSCKASGYTFTSHWMHWVKQRAGQGLEWIGEFNPSNGRTN
YNEKFKSKATLTVDKSSSTAYMQLSSLTSEDSAVYYCASRDYDYDGRYFDYWGQGTTVTVSSG
GGGSGGGGSGGGGSDIELTQSPAIMSASPGEKVTMTCSASSSVTYMYWYQQKPGSSPRLLIYDT
SNLASGVPVRFSGSGSGTSYSLTISRMEAEDAATYYCQQWSSHIFTFGSGTELEIKRAAAGGGGS
ALALPLSSIFSRIGDPGGPYVHDEVDRGPPGSRMDKDCEMKRTTLDSPLGKLELSGCEQGLHEI
KLLGKGTSAADAVEVPAPAAVLGGPEPLMQATAWLNAYFHQPEAIEEFPVPALHHPVFQQESF
TRQVLWKLLKVVKFGEVISYQQLAALAGNPAATAAVKTALSGNPVPILIPCHRVVSSSGAVGGY
EGGLAVKEWLLAHEGHRLGKP

SEQUENCE LISTING

```
<160> NUMBER OF SEQ ID NOS: 3

<210> SEQ ID NO 1
<211> LENGTH: 245
<212> TYPE: PRT
<213> ORGANISM: homo sapiens

<400> SEQUENCE: 1

Met Ala Gln Val Gln Leu Gln Gln Ser Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Ser His Trp Met His Trp Val Lys Gln Arg Ala Gly Gln Gly Leu Glu
        35                  40                  45

Trp Ile Gly Glu Phe Asn Pro Ser Asn Gly Arg Thr Asn Tyr Asn Glu
    50                  55                  60

Lys Phe Lys Ser Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Ser Arg Asp Tyr Asp Tyr Asp Gly Arg Tyr Phe Asp Tyr
            100                 105                 110

Trp Gly Gln Gly Thr Thr Val Thr Val Ser Ser Gly Gly Gly Gly Ser
        115                 120                 125

Gly Gly Gly Gly Ser Gly Gly Gly Ser Asp Ile Glu Leu Thr Gln
    130                 135                 140

Ser Pro Ala Ile Met Ser Ala Ser Pro Gly Glu Lys Val Thr Met Thr
145                 150                 155                 160

Cys Ser Ala Ser Ser Ser Val Thr Tyr Met Tyr Trp Tyr Gln Gln Lys
                165                 170                 175

Pro Gly Ser Ser Pro Arg Leu Leu Ile Tyr Asp Thr Ser Asn Leu Ala
            180                 185                 190

Ser Gly Val Pro Val Arg Phe Ser Gly Ser Gly Ser Gly Thr Ser Tyr
        195                 200                 205

Ser Leu Thr Ile Ser Arg Met Glu Ala Glu Asp Ala Ala Thr Tyr Tyr
    210                 215                 220

Cys Gln Gln Trp Ser Ser His Ile Phe Thr Phe Gly Ser Gly Thr Glu
225                 230                 235                 240

Leu Glu Ile Lys Arg
                245

<210> SEQ ID NO 2
<211> LENGTH: 179
<212> TYPE: PRT
<213> ORGANISM: Artificial Sequence
<220> FEATURE:
<223> OTHER INFORMATION: SNAP-tag

<400> SEQUENCE: 2
```

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
                20                  25                  30

Leu Leu Gly Lys Gly Thr Ser Ala Ala Asp Ala Val Glu Val Pro Ala
            35                  40                  45

Pro Ala Ala Val Leu Gly Gly Pro Glu Pro Leu Met Gln Ala Thr Ala
50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
                100                 105                 110

Ser Tyr Gln Gln Leu Ala Ala Leu Ala Gly Asn Pro Ala Ala Thr Ala
                115                 120                 125

Ala Val Lys Thr Ala Leu Ser Gly Asn Pro Val Pro Ile Leu Ile Pro
            130                 135                 140

Cys His Arg Val Val Ser Ser Gly Ala Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro

<210> SEQ ID NO 3
<211> LENGTH: 465
<212> TYPE: PRT
<213> ORGANISM: Artificial Sequence
<220> FEATURE:
<223> OTHER INFORMATION: Fusionprotein

<400> SEQUENCE: 3

Met Ala Gln Val Gln Leu Gln Gln Ser Gly Ala Glu Leu Val Lys Pro
1               5                   10                  15

Gly Ala Ser Val Lys Leu Ser Cys Lys Ala Ser Gly Tyr Thr Phe Thr
                20                  25                  30

Ser His Trp Met His Trp Val Lys Gln Arg Ala Gly Gln Gly Leu Glu
            35                  40                  45

Trp Ile Gly Glu Phe Asn Pro Ser Asn Gly Arg Thr Asn Tyr Asn Glu
50                  55                  60

Lys Phe Lys Ser Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Ser Arg Asp Tyr Asp Tyr Asp Gly Arg Tyr Phe Asp Tyr
                100                 105                 110

Trp Gly Gln Gly Thr Thr Val Thr Val Ser Ser Gly Gly Gly Gly Ser
            115                 120                 125

Gly Gly Gly Gly Ser Gly Gly Gly Ser Asp Ile Glu Leu Thr Gln
            130                 135                 140

Ser Pro Ala Ile Met Ser Ala Ser Pro Gly Glu Lys Val Thr Met Thr
145                 150                 155                 160

Cys Ser Ala Ser Ser Ser Val Thr Tyr Met Tyr Trp Tyr Gln Gln Lys
                165                 170                 175

Pro Gly Ser Ser Pro Arg Leu Leu Ile Tyr Asp Thr Ser Asn Leu Ala
```

```
            180                 185                 190

Ser Gly Val Pro Val Arg Phe Ser Gly Ser Gly Ser Gly Thr Ser Tyr
        195                 200                 205

Ser Leu Thr Ile Ser Arg Met Glu Ala Glu Asp Ala Ala Thr Tyr Tyr
        210                 215                 220

Cys Gln Gln Trp Ser Ser His Ile Phe Thr Phe Gly Ser Gly Thr Glu
225                 230                 235                 240

Leu Glu Ile Lys Arg Ala Ala Gly Gly Gly Ser Ala Leu Ala
                245                 250                 255

Leu Pro Leu Ser Ser Ile Phe Ser Arg Ile Gly Asp Pro Gly Gly Pro
                260                 265                 270

Tyr Val His Asp Glu Val Asp Arg Gly Pro Pro Gly Ser Arg Met Asp
                275                 280                 285

Lys Asp Cys Glu Met Lys Arg Thr Thr Leu Asp Ser Pro Leu Gly Lys
        290                 295                 300

Leu Glu Leu Ser Gly Cys Glu Gln Gly Leu His Glu Ile Lys Leu Leu
305                 310                 315                 320

Gly Lys Gly Thr Ser Ala Ala Asp Ala Val Glu Val Pro Ala Pro Ala
                325                 330                 335

Ala Val Leu Gly Gly Pro Glu Pro Leu Met Gln Ala Thr Ala Trp Leu
                340                 345                 350

Asn Ala Tyr Phe His Gln Pro Glu Ala Ile Glu Glu Phe Pro Val Pro
                355                 360                 365

Ala Leu His His Pro Val Phe Gln Gln Glu Ser Phe Thr Arg Gln Val
                370                 375                 380

Leu Trp Lys Leu Leu Lys Val Val Lys Phe Gly Glu Val Ile Ser Tyr
385                 390                 395                 400

Gln Gln Leu Ala Ala Leu Ala Gly Asn Pro Ala Ala Thr Ala Ala Val
                405                 410                 415

Lys Thr Ala Leu Ser Gly Asn Pro Val Pro Ile Leu Ile Pro Cys His
                420                 425                 430

Arg Val Val Ser Ser Ser Gly Ala Val Gly Gly Tyr Glu Gly Gly Leu
                435                 440                 445

Ala Val Lys Glu Trp Leu Leu Ala His Glu Gly His Arg Leu Gly Lys
        450                 455                 460

Pro
465
```

SPECIFIC PHOTOIMMUNO-THERANOSTICS FOR DETECTION AND ELIMINATION OF SKIN CANCER CELLS

CROSS REFERENCE TO RELATED APPLICATIONS

This is a US national phase application under 35 USC § 371 of international patent application no. PCT/EP2015/063422, filed Jun. 16, 2015; the content of which is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with file "PCTEP2015063422_2017_12_SEQID" created on 11 Dec. 2017, filed on 12 Dec. 2017 and having a size of 8 Kilobytes. The sequence listing contained in this ASCII formatted document forms part of the specification and is herein incorporated by reference in its entirety.

FIELD OF THE INVENTION

The technology provided herein generally relates to novel specific photoimmuno-theranostics for the use in detection and elimination of skin cancer cells.

The technology also relates to novel methods which generate homogeneous and specific photoimmuno-theranostics reagents in a simple, controlled and efficient way. This method combines molecular optical imaging, photodynamic therapy and immunotherapy using SNAP-tag technology.

BACKGROUND OF THE INVENTION

The term "theranostics" was first introduced by Funkhouser in 2002 and defines a reagent that combines both diagnostic as well as therapeutic aspects. Theranostics are mostly used in cancer therapies and are widely believed to have a considerable impact on healthcare before, during and after disease by improving cancer prognosis and management simultaneously.

Current theranostics approaches still rely on unspecific passive tumor targeting strategies, which have a scattergun effect and tend to damage both neoplastic and non-neoplastic cells.

This is in contrast to the theranostics of the technology provided herein, which generates highly homogeneous, standardized and pharmaceutically acceptable photoimmuno-conjugates in a controlled way. Thus, the photoimmuno-theranostic reagents produced by the methods according to the present disclosure possess a homogenized pharmacokinetic and bio-distribution property not known in the prior art.

Currently, skin cancers are the most commonly diagnosed forms of human cancer worldwide, and more than 3.5 million new cases are diagnosed per year in USA. During recent years, significant progress has been achieved to improve skin cancer prognosis and management. Still, the incidence and mortality rate of melanoma and non-melanoma skin cancer has been increased over the past decades.

One therapeutic option against non-melanoma skin cancer is photodynamic therapy (PDT). PDT holds great promise for improving non-melanoma skin cancer treatment; several photosensitizers have been approved for use in humans such as porfimer sodium (Photofrin), meta-tetrahydroxyphenyl-chlorin (Foscan) and 5-aminolevulinic acid (Metvix).

Thus far, tumor targeting in PDT management relies on passive accumulation of photosensitizers in tumor tissues, which can limit the success of PDT. Moreover, these forms of photosensitization can also damage healthy tissue and result in prolonged skin photosensitivity.

The considerable growth in understanding molecular mechanisms of cancer development has paved the way for developing targeted therapies addressing key disease biomarkers. Therefore, combining targeted therapies with PDT resulted in so-called photo-immunotherapy (PIT).

Based on this principle, different photosensitizers have been conjugated to cell specific monoclonal antibodies and their derivatives that can be used to specifically target certain neoplastic cell populations. Furthermore, the imaging properties of some photosensitizers can be exploited for diagnostic use, i.e. to pre-screen tumors, monitor photosensitizer tissue accumulation and quantify treatment effectiveness.

Although PIT has been proposed since 1995 to treat malignant skin cancers, and several photosensitizers as well as antibodies have been approved individually for the treatment of human patients, PIT has not entered the stage of clinical use so far.

This is mainly due to failure in generating highly homogeneous, standardized and pharmaceutically acceptable photoimmuno-conjugates, since random conjugation methods were mainly used to arm antibodies with photosensitizer molecules.

The technology presented hereinunder uses self-labeling proteins such as SNAP-tag which provide a simple solution for controlled and robust conjugation of proteins with many various chemical entities under physiological conditions with high efficacy and a 1:1 stoichiometry.

SUMMARY OF THE INVENTION

The technology provided herein relates to novel photoimmuno-theranostics reagents as well as methods which generate homogeneous and specific photoimmuno-theranostics reagents in a simple, controlled and efficient way. This method combines molecular optical imaging, photodynamic therapy and immunotherapy using SNAP-tag technology.

The technology provided herein relates to an immuno-theranostics approach which was developed for targeting epidermal growth factor receptor (EGFR) expressing skin cancer cells by conjugating IRDye®700DX N-hydroxysuccinimide ester (IR700) photosensitizer to a single-chain variable fragment antibody against EGFR (scFv-425) using SNAP-tag technology.

In one aspect, the present disclosure pertains to photoimmuno-theranostic reagents described by formula 1:

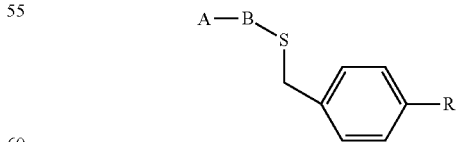

wherein moiety A is at least 80%, preferably 85%, preferably 90%, more preferably 95% identical to the sequences selected of SEQ ID No. 1, and wherein moiety B is at least 95% preferably 96%, preferably 97%, preferably 98%, more preferably 99% identical to the sequences selected of SEQ ID No. 2; and wherein moiety R is selected from a group of photosensitizers comprising a fluorescent dye, N-hydroxysuccinimide ester (IR700), porfimer sodium (Photofrin), meta-tetrahydroxyphenylchlorin (Foscan), 5-aminolevulinic acid (Metvix) and Benzoporphyrin derivative, and/or nanotheranostics reagents.

EGFR is a transmembrane receptor that is expressed at high levels in many cancers, including skin cancers. This targeted approach shows high specificity, efficacy and safety for both the detection and destruction of skin cancer cells in vitro.

Recently, N-hydroxysuccinimide ester (IR700; also known under the trademark IRDye®700DX) photosensitizer has been described as a promising photosensitizer due to its ideal properties such as the high purity and the strong absorption peak at 689 nm that allowing a deeper light penetration into tissues. Furthermore, IR700 is also not up-taken by cells; therefore it is considered safe even after illumination.

The SNAP-tag is an engineered human DNA repair enzyme, alkylguanine-DNA alkyltransferase, and has the ability to specifically catch O(6)-benzylguanine (BG)-modified substrates via irreversible coupling of a benzyl group to a cysteine residue. This method was originally developed to label fusion proteins with fluorescent dyes and has been adapted to site-specifically conjugate various therapeutic molecules such as photosensitizers and drug nanocarriers The reagent generated herein can be used to simultaneously detect, diagnose, monitor, suppress and treat the growth of skin cancer cell lines expressing epidermal growth factor receptor (EGFR): It was possible to specifically recognize different EGFR-expressing skin cancer cell lines and eliminate them at EC50's of 32-55 nM.

BRIEF DESCRIPTION OF THE DRAWINGS

FIG. 8 shows the amino acid sequences of the single-chain variable fragment antibody against EGFR (scFv-425) (SEQ ID No. 1), the amino acid sequence of the SNAP-tag element (SEQ ID No. 2) and the scFv-425-SNAP-tag amino acid sequence (SEQ ID No. 2).

DETAILED DESCRIPTION OF THE INVENTION

Figure 1:
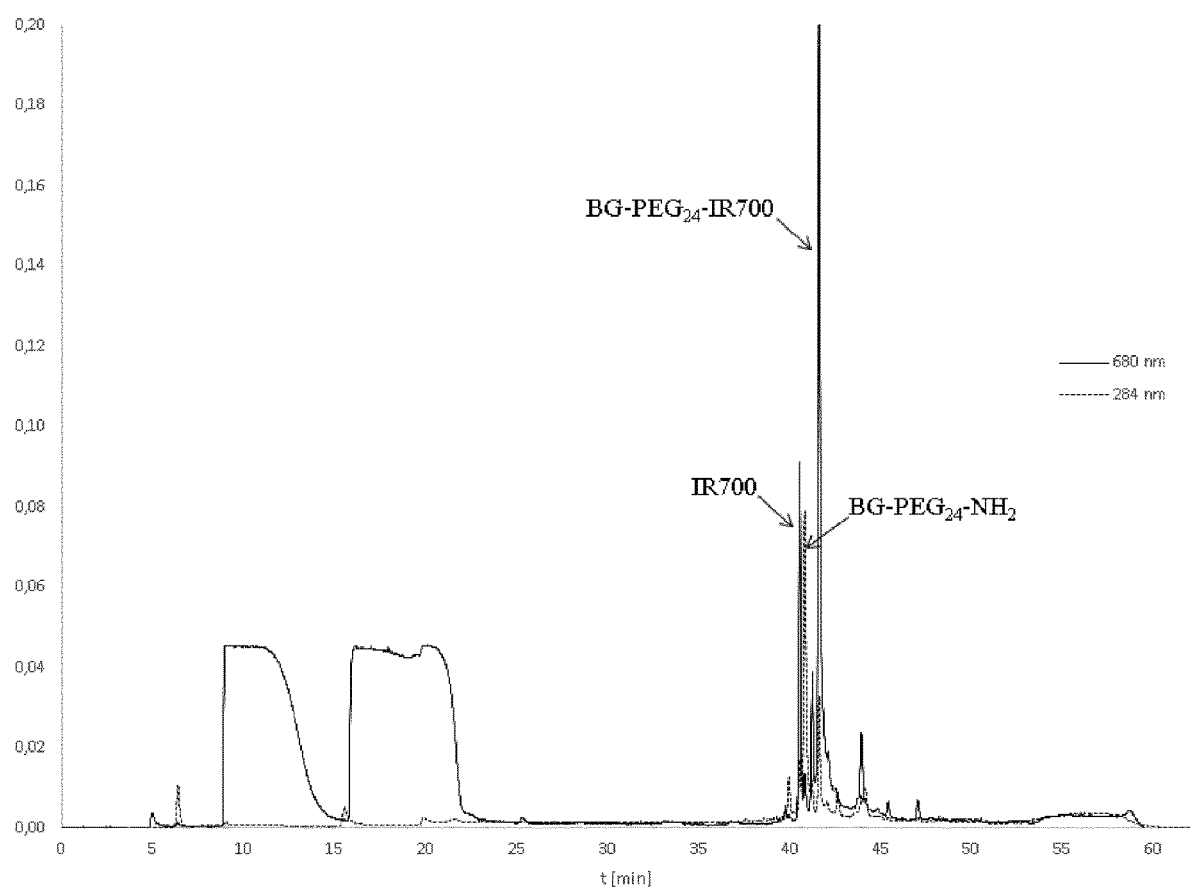
FIG. 1 shows the HPLC purification profile of BG-PEG$_{24}$-IR700. BG-modified IR700 was purified using Prontosil C-18 (250×4.6 mm, 5 µm, 120 Å) column and a flow rate of 1 mL/min. Monitoring occurred at wavelength of 286 (broken lined curve) and 680 nm (continuous lined curve).

The present disclosure pertains to generate highly homogeneous photoimmuno-theranostic reagents with standardized pharmacokinetic and therapeutic profiles.

In detail the present disclosure pertains to a photoimmuno-theranostics reagent described by formula 1:

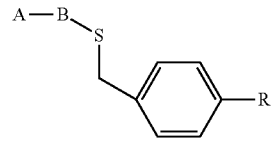

wherein moiety A is at least 80% identical the sequence of SEQ ID No. 1;
wherein moiety B is at least 95% identical the sequences of SEQ ID No. 2;
wherein moiety R is selected from a group of photosensitizers comprising IR700 (IRDye®700DX N-hydroxysuccinimide ester), porfimer sodium (Photofrin), meta-tetrahydroxyphenylchlorin (Foscan), 5-aminolevulinic acid (Metvix) and a fluorescent dye like Alexa-647, and/or a drug nanocarrier.

In one disclosure moiety A (SEQ ID No. 1) is an antibody which binds to EGFR.

In another disclosure moiety A is a single-chain variable fragment antibody against EGFR and/or comprises an amino acid sequence at least 80%, 85%, 90%, 95%, 99%, 100% identical to the sequence of SEQ ID No. 1.

In another disclosure moiety B is a SNAP-tag amino and/or comprises an amino acid sequence at least 80%, 85%, 90%, 95%, 99%, 100% identical to the sequence of SEQ ID No. 2.

The term "antibody," as used herein, refers to immunoglobulin molecules and immunologically active portions of immunoglobulin molecules, i.e., molecules that contain an antigen binding site that immunospecifically binds an antigen. The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein.

"Fab fragments" (fragment antigen-binding) comprise a region on an antibody that binds to antigens. They are composed of one constant and one variable domain of each of the heavy and the light chain. These domains shape the paratope—the antigen-binding site—at the amino terminal end of the monomer. The two variable domains bind the epitope on their specific antigens. The variable regions of the heavy and light chains can be fused together to form a single-chain variable fragment (scFv), which is only half the size of the Fab fragment, yet retains the original specificity of the parent immunoglobulin.

Fab and F(ab')2 fragments lack the Fc fragment of intact antibody, clear more rapidly from the circulation of the human, animal and/or plant, and may have less non-specific tissue binding than an intact antibody. Thus, these fragments are preferred, as well as the products of a FAB and/or single-chain variable fragment (scFv) antibodies.

Moreover, antibodies of the present disclosure include chimeric and humanized antibodies.

In one disclosure the antibodies are human antigen-binding antibody fragments of the present disclosure and include, but are not limited to, Fab, Fab' and F(ab')2, Fd, single-chain Fvs (scFv), single-chain antibodies, disulfide-linked Fvs (sdFv) and fragments comprising either a VL or VH domain.

Antigen-binding antibody fragments, including single-chain antibodies, may comprise the variable region(s) alone or in combination with the entirety or a portion of the following: hinge region, CH1, CH2, and CH3 domains. Also included in the present disclosure are antigen-binding fragments also comprising any combination of variable region(s) with a hinge region, CH1, CH2, and CH3 domains. The antibodies of the disclosure may be from any human or animal origin including birds and mammals. In one disclosure, the antibodies are human, murine (e.g., mouse and rat), donkey, ship rabbit, goat, guinea pig, camel, horse, or chicken.

As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins.

The antibodies of the present disclosure may be mono-specific, bispecific, trispecific or of greater multispecificity. Multispecific antibodies may be specific for different epitopes of a polypeptide of the present disclosure or may be specific for both a polypeptide of the present disclosure as well as for a heterologous epitope, such as a heterologous polypeptide or solid support material.

Antibodies of the present disclosure may be described or specified in terms of the epitope(s) or portion(s) of an EGFR-derived polypeptide of the present disclosure which they recognize or specifically bind.

The term "EGFR" relates herein to epidermal growth factor receptor. This is a transmembrane glycoprotein that is a member of the protein kinase superfamily. This protein is a receptor for members of the epidermal growth factor family. EGFR is a cell surface protein that binds to epidermal growth factor. Binding of the protein to a ligand induces receptor dimerization and tyrosine autophosphorylation and leads to cell proliferation. Mutations in this gene are associated with different forms of cancer, e.g. skin tumors (e.g. cutaneous squamous cell carcinoma (SCC)) and lung cancer. Multiple alternatively spliced transcript variants that encode different protein isoforms have been found for this gene. In some disclosures of the present invention the antibody is selective for mutated forms of EGFR or EGFR-derived polypeptides.

Wherein the term "EGFR-derived polypeptide" refers to polypeptides comprising the complete sequences of EGFR, mutations of EGFR and/or fragments thereof, but also to ligands of EGFR (e.g. any member of the members of the epidermal growth factor family) or fragments of such ligands, as well as polypeptides which can be identified upstream and downstream of the EGFR-activation pathway.

For the purposes of the disclosure, "immunizing agent" may be defined as an EGFR-derived polypeptide of the disclosure, including fragments, variants, and/or derivatives thereof, in addition to fusions with heterologous polypeptides and other forms of the EGFR-derived polypeptides described herein.

Antibodies of the present disclosure may also be described or specified in terms of their cross-reactivity. Antibodies that do bind any other analog, ortholog, or homologue of a EGFR-derived polypeptide of the present disclosure are included. Antibodies that bind EGFR-derived polypeptide with at least 95%, at least 90%, at least 85%, at least 80%, at least 75%, at least 70%, at least 65%, at least 60%, at least 55%, and at least 50% identity (as calculated using methods known in the art and described herein) to an EGFR-derived polypeptide of the present disclosure are also included in the present disclosure. In specific embodiments, antibodies of the present disclosure cross-react with murine, rat and or rabbit homologues of human proteins and the corresponding epitopes thereof.

Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art) to an EGFR-derived polypeptide of the present disclosure are excluded in the present disclosure. In a specific embodiment, the above-described cross-reactivity is with respect to any single specific antigenic or immunogenic polypeptide, or combination(s) of 2, 3, 4, 5, or more of the specific antigenic and/or immunogenic EGFR-derived polypeptide disclosed herein.

Further included in the present disclosure are antibodies which bind EGFR-derived polypeptides encoded by polynucleotides which hybridize to a polynucleotide of the present disclosure under stringent hybridization conditions (as described herein). Antibodies of the present disclosure may also be described or specified in terms of their binding affinity to an EGFR-derived polypeptide of the disclosure.

Preferred binding affinities include those with a dissociation constant or $K_d$ less than $5\times10^{-2}$ M, $5\times10^{-3}$ M, $5\times10^{-4}$ M, $5\times10^{-5}$ M, $5\times10^{-6}$ M, $5\times10^{-7}$ M, $5\times10^{-8}$ M, $5\times10^{-9}$ M, $5\times10^{-10}$ M, $5\times10^{-11}$ M, $5\times10^{-12}$ M, $5\times10^{-13}$ M, $5\times10^{-14}$ M or $5\times10^{-15}$ M.

The disclosure also provides antibodies that competitively inhibit binding of a second antibody to an EGFR-derived polypeptide epitope of the disclosure as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present disclosure may act as agonists or antagonists of the EGFR-derived polypeptides of the present disclosure. For example, the present disclosure includes antibodies which disrupt the receptor/ligand interactions with the EGFR either partially or fully. In one disclosure, antibodies of the present disclosure bind an antigenic epitope disclosed herein, or a portion thereof. The disclosure also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immuno-precipitation followed by western blot analysis. In specific disclosures, antibodies are provided that inhibit ligand activity or receptor activity by at least 95%, at least 90%, at least 85%, at least 80%, at least 75%, at least 70%, at least 60%, or at least 50% of the activity in absence of the antibody. The disclosure also features EGFR-specific antibodies which both prevent ligand binding and receptor activation as well as antibodies that recognize the receptor-ligand complex, and, in one disclosure, do not specifically recognize the unbound receptor or the unbound ligand. Likewise, included in the disclosure are neutralizing antibodies which bind the EGFR ligand and prevent binding of the EGFR ligand to the receptor, as well as antibodies which bind the EGFR ligand, thereby preventing receptor activation, but do not prevent the EGFR ligand from binding the receptor.

Antibodies of the present disclosure may be used, for example, but not limited to, to purify, detect, diagnose, monitor, treat, suppress activity, anatogonize and target the EGFR-derived polypeptides of the present disclosure, including both in vitro and in vivo diagnostic and therapeutic methods. For example, the antibodies have use in immunoassays for qualitatively and quantitatively measuring levels of the polypeptides of the present disclosure in biological samples.

The antibodies of the present disclosure may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present disclosure may be recombinantly fused or conjugated to molecules useful as labels in detection assays and effector molecules such as heterologous polypeptides, drugs, radionuclides, or toxins.

The antibodies of the disclosure include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present disclosure may be generated by any suitable method known in the art.

The antibodies of the present disclosure may comprise polyclonal antibodies.

In one disclosure the present disclosure pertains to a preparation and purification of an EGFR-derived polypeptide, to render it substantially free of natural contaminants. Such a preparation is then introduced into an animal in order to produce polyclonal antisera of greater specific activity.

For example, an EGFR-derived polypeptide of the disclosure can be administered to various host animals including, but not limited to, rabbits, mice, rats, etc. to induce the production of sera containing polyclonal antibodies specific for the antigen. The administration of the polypeptides of the present disclosure may entail one or more injections of an immunizing agent and, if desired, an adjuvant. Various adjuvants may be used to increase the immunological response, depending on the host species, and include but are not limited to, Freund's (complete and incomplete), mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Typically, the immunizing agent and/or adjuvant will be injected in the mammal by multiple subcutaneous or intra-peritoneal injections, though they may also be given intramuscularly, and/or through IV). The immunizing agent may include polypeptides of the present disclosure or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivatizing active chemical functional groups to both the polypeptide of the present disclosure and the immunogenic protein such that a covalent bond is formed, or through fusion-protein based methodology, or other methods known to the skilled artisan.

Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present disclosure may comprise monoclonal antibodies.

Monoclonal antibodies may be prepared using hybridoma methods, such as those described in Antibodies: A Labaratory Manual, (Cold spring Harbor Labaratory Press, 4th ed. (2014), by Hammerling, et al., or other methods known to the artisan.

Other examples of methods which may be employed for producing monoclonal antibodies includes, but are not limited to, the human B-cell hybridoma technique and the EBV-hybridoma technique.

Such antibodies may be of any immunoglobulin class including IgG, IgM, IgE, IgA, IgD and any subclass thereof. The hybridoma producing the mAb of this disclosure may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include EGFR-derived polypeptides. In one disclosure, the immunizing agent consists of an EGFR-derived polypeptide or, in one disclosure, with an EGFR-derived polypeptide-expressing cell.

Such cells may be cultured m any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that in one disclosure contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred the parent myeloma cell line (SP20) as provided by the ATCC®.

As inferred throughout the specification, human myeloma and mouse-human heteromyeloma cell lines for the production of human monoclonal antibodies are known in the art.

The culture medium in which the hybridoma cells are cultured can then be assayed for the presence of monoclonal antibodies directed against the polypeptides of the present disclosure. In one disclosure, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA).

After the desired hybridoma cells are identified, the clones may be subcloned by limiting dilution procedures and grown by standard methods. Suitable culture media for this purpose include, for example, Dulbecco's Modified Eagle's Medium and RPMI-1640.

Alternatively, the hybridoma cells may be grown in vivo as well as in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the disclosure is not limited to their sole production in hybridomas. For example, the monoclonal antibodies may be made by recombinant DNA methods. In this context, the term "monoclonal antibody" refers to an antibody derived from a single eukaryotic, phage, or prokaryotic clone. The DNA encoding the monoclonal antibodies of the disclosure can be readily isolated and sequenced using conventional procedures (e.g., by using oligonucleotide probes that are capable of binding specifically to genes encoding the heavy and light chains of murine antibodies, or such chains from human, humanized, or other sources).

The hybridoma cells of the disclosure serve as a preferred source of such DNA.

Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences or by covalently joining to the immunoglobulin coding sequence all or part of the coding sequence for a non-immunoglobulin polypeptide. Such a non-immunoglobulin polypeptide can be substituted for the constant domains of an antibody of the disclosure, or can be substituted for the variable domains of one antigen-combining site of an antibody of the disclosure to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc-region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the disclosure or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC®. Hybridomas are selected and cloned by limited dilution. The hybridoma clones are then assayed by methods known in the art for cells that secrete antibodies capable of binding a polypeptide of the disclosure. Ascites fluid, which generally contains high levels of antibodies, can be generated by immunizing mice with positive hybridoma clones.

Accordingly, the present disclosure provides methods of generating monoclonal antibodies as well as antibodies produced by the method comprising culturing a hybridoma cell secreting an antibody of the disclosure wherein, In one disclosure, the hybridoma is generated by fusing splenocytes isolated from a mouse immunized with an antigen of the disclosure with myeloma cells and then screening the hybridomas resulting from the fusion for hybridoma clones that secrete an antibody able to bind a polypeptide of the disclosure.

Antibody fragments which recognize specific epitopes may be generated by known techniques. For example, Fab and F(ab')2 fragments of the disclosure may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present disclosure can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present disclosure include those disclosed are known in the prior art.

After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below.

Examples of techniques which can be used to produce single-chain Fvs and antibodies include those described in Huston et al., Methods in Enzymology 203:46-88 (1991); Shu et al., PNAS 90:7995-7999 (1993); and Skerra et al., Science 240:1038-1040 (1988).

For some uses, including in-vivo use of antibodies in humans and in vitro detection assays, it may be preferable to use chimeric, humanized, or human antibodies.

A chimeric antibody is a molecule in which different portions of the antibody are derived from different animal species, such as antibodies having a variable region derived from a murine monoclonal antibody and a human immunoglobulin constant region.

Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, in one disclosure improve, antigen binding. These framework Substitutions are identified by methods well known in the art, e.g., by modeling of the interactions of the CDR and framework residues to identify framework residues important for antigen binding and sequence comparison to identify unusual framework residues at particular positions.

Antibodies can be humanized using a variety of techniques known in the art including, for example, CDR-grafting, veneering or resurfacing and chain shuffling.

Generally, a humanized antibody has one or more amino acid residues introduced into it from a source that is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fe), typically that of a human immunoglobulin.

Completely human antibodies are desirable for therapeutic treatment of human patients. Human antibodies can be made by a variety of methods known in the art including phage display methods described above using antibody libraries derived from human immunoglobulin sequences.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells.

Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the disclosure. Monoclonal antibodies directed against the antigen can be obtained from the immunized, transgenic mice using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM. and IgE antibodies.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire.

Completely human antibodies which recognize a selected epitope can be generated using a technique referred to as "guided selection." In this approach a selected nonhuman monoclonal antibody, e.g., a mouse antibody, is used to guide the selection of a completely human antibody recognizing the same epitope.

Further, antibodies to the polypeptides of the disclosure can, in turn, be utilized to generate anti-idiotype antibodies that "mimic" EGFR-derived polypeptides of the disclosure using techniques well known to those skilled in the art.

For example, antibodies which bind to and competitively inhibit polypeptide multimerization and/or binding of a polypeptide of the disclosure to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the disclosure and/or to bind its ligands/receptors, and thereby block its biological activity.

Such anti-idiotypic antibodies capable of binding to an EGFR-derived polypeptide can be produced in a two-step procedure. Such a method makes use of the fact that antibodies are themselves antigens, and therefore, it is possible to obtain an antibody that binds to a second antibody.

In accordance with this method, protein specific antibodies are used to immunize an animal, in one disclosure a mouse. The splenocytes of such an animal are then used to produce hybridoma cells, and the hybridoma cells are screened to identify clones that produce an antibody whose ability to bind to the protein-specific antibody can be blocked by the polypeptide. •such antibodies comprise anti-idiotypic antibodies to the protein-specific antibody and can be used to immunize an animal to induce formation of further protein-specific antibodies.

The antibodies of the present disclosure may be bispecific antibodies. Bispecific antibodies are monoclonal, In one disclosure human or humanized, antibodies that have binding specificities for at least two different antigens. In the present disclosure, one of the binding specificities may be directed towards a polypeptide of the present disclosure~ the other may be for any other antigen, and In one disclosure for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain light-chain pairs, where the two heavy chains have different specificities. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps.

Antibody variable domains with the desired binding specificities (antibody antigen combining sites) can be fused to immunoglobulin constant domain sequences. The fusion In one disclosure is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism.

Heteroconjugate antibodies are also contemplated by the present disclosure.

Heteroconjugate antibodies are composed of two covalently joined antibodies. Such antibodies have, for example, been proposed to target immune system cells to unwanted cells. It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate.

In one disclosure of the present invention moiety B is at least 95%, 96%, 97%, 98%, 99%, 100% identical to one of the sequences selected SEQ ID No. 2.

In another disclosure moiety B is a SNAP-tag polypeptide.

"SNAP-tag" is a self-labeling protein tag commercially available in various expression vectors. SNAP-tag is a 182 residues polypeptide (19.4 kDa) that can be fused to any protein of interest and further specifically and covalently tagged with a suitable ligand, such as a fluorescent dye.

Since its introduction, SNAP-tag has found numerous applications in biochemistry and for the investigation of the function and localisation of proteins and enzymes in living cells. Compared to the current standard labelling methods used in fluorescence microscopy, the use of SNAP-tag presents the significant advantage in being high specific for its substrate.

The SNAP-tag protein is an engineered version of the ubiquitous mammalian enzyme AGT, encoded in humans by the O-6-methylguanine-DNA methyltransferase (MGMT) gene. SNAP-tag was obtained using a directed evolution strategy, leading to a hAGT variant that accepts O6-benzylguanine derivatives instead of repairing alkylated guanine derivatives in damaged DNA.

Apart from fluorescence microscopy, SNAP-tag has proven useful in the elucidation of numerous biological processes, including the identification of multiprotein complexes using various approaches such as FRET, cross-linking, proximity ligation assay. Other application include the measurement of protein half-lives in vivo, and small molecule-protein interactions.

As disclosed herein fusion proteins were derived from the binding function of an antibody fused with a SNAP-tag. The AGT recognizes highly specific Benzylguanine-modified (BG) substrates and forms in a catalytic reaction a covalent bond to it.

The so antibody-fragment-SNAP-tag-fusion proteins (moieties A and B in formula 1) produced by the methods of the present disclosure can then be used to specifically bind to BG-modified molecules. Thereby, the high specificity of the AGT-fusion protein for alkylated substances enables the efficient covalent and stoichiometric coupling of low molecular weight substances under physiological conditions.

With the methods disclosed herein, BG-modified substrates are covalently attached by the irreversible coupling of an alkyl group to a cysteine residue. This way, ligands are attached in an efficient, rapid and site-specific fashion with 1:1 stoichiometry; this method has been found to yield reproducible results for labeling proteins with various BG-modified molecules, ranging from small molecules such as photosensitizers to large molecules such as drug nanocarriers.

In one disclosure the benzylguanine linker is selected from the group consisting of $BG-NH_2$ and $BG-PEG_{24}-NH_2$. In another disclosure the linker is selected from any one of the linkers disclosed in table 1.

The term "benzylguanine linker" refers to any linkage of the core benzylguanine (BG) moieties to activated esters, primary amines and thiol groups. Examples known in the prior art are depicted in table 1.

TABLE 1

Examples for potential benzylguanine linker

| Product | Structure | Application |
|---|---|---|
| BG-NH2 | 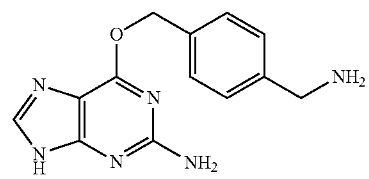 [SMILES: NCc1ccc(COc2nc(N)nc3[nH]cnc23)cc1] | SNAP-tag substrate. Suitable for linkage to NHS esters and other activated carboxylic esters. |
| BG-PEG—NH2 | 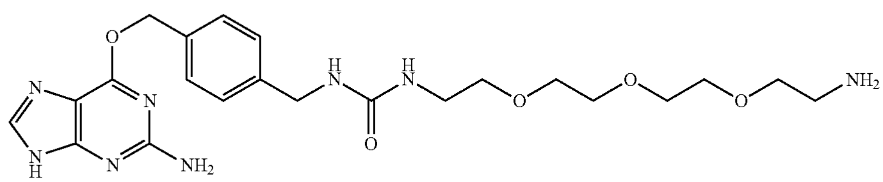 [SMILES: NCCOCCOCCOCCNC(=O)NCc1ccc(COc2nc(N)nc3[nH]cnc23)cc1] | SNAP-tag substrate. PEG-linker gives superior flexibility. Particularly suited for immobilization on solid surfaces. |
| BG-GLA-NHS | 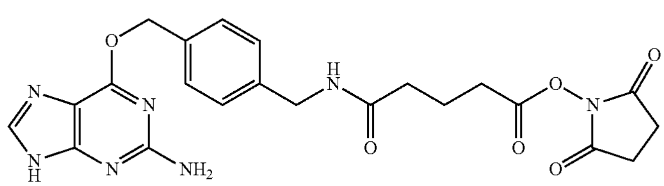 [SMILES: Nc1nc(OCc2ccc(CNC(=O)CCCC(=O)ON3C(=O)CCC3=O)cc2)c2nc[nH]c2n1] | SNAP-tag substrate. Activated as NHS ester. Reacts with primary amines. |
| BG-Maleimide | 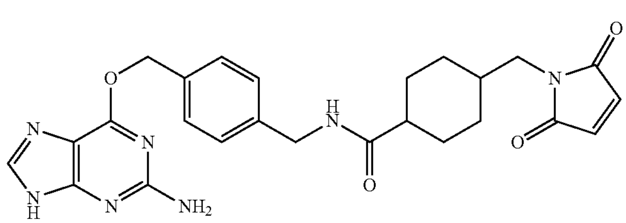 [SMILES: Nc1nc(OCc2ccc(CNC(=O)C3CCC(CN4C(=O)C=CC4=O)CC3)cc2)c2nc[nH]c2n1] | SNAP-tag substrate. Activated as maleimide. Reacts with thiols. |

The present disclosure also pertains to a method for producing a high specific photoimmuno-theranostics reagent, comprising the steps of:
a. Expression and purification of an antibody against EGFR-derived polypeptide;
b. Fusion of the antibody of step a.) with a SNAP-tag;
c. Modification of a therapeutically and/or diagnostically active substance with a benzylguanine linker;
d. Conjugation of the antibody against the EGFR-derived polypeptide of step a.) with the benzylguanine linker-modified therapeutically and/or diagnostically active substance of step c.) in a one-step reaction;
wherein the resulting fusion protein is suitable for the use as a photoimmuno-theranostics reagent.

In one disclosure the method for producing a high specific photoimmuno-theranostics reagent comprises the steps of:
a. Expression and purification of a single-chain variable antibody fragment against EGFR;
b. Fusion of the single-chain variable antibody fragment of step a.) with a SNAP-tag;
c. Modification of a therapeutically and/or diagnostically active substance with a benzylguanine linker;
d. Conjugation of the single-chain variable fragment antibody against EGFR of step a.) with the benzylguanine linker-modified therapeutically and/or diagnostically active substance of step c.) in a one-step reaction;
wherein the resulting fusion protein is suitable for the use as a photoimmuno-theranostics reagent.

Wherein the term "theranostics reagent" relates to any reagent which is both suitable for detection, diagnostic and/or the treatment of a disease or condition of a patient. The term "photoimmuno-theranostics reagent" therefore relates to theranostics which comprise both a photoreactive part as well as an immunologic part.

The term "photoreactive part" refers to any moiety which responds with a chemical reaction upon light excitation, for example such as photosensitizer and/or drug nanocarriers. The term "immunologic part" refers to any chemical entity able to bind to antigens, for example such as any antibody as defined hereinunder, or any other antigen binding entity, for example anticalins and the like.

The term "therapeutically and/or diagnostically active substance" relates to any moiety which responds with a chemical reaction upon light excitation, for example such as photosensitizers and/or drug nanocarriers.

In one disclosure of the invention moiety R of formula 1 is selected from a group of photosensitizers comprising N-hydroxysuccinimide ester (IR700; also known as IRDye®700DX), porfimer sodium (Photofrin), meta-tetrahydroxyphenylchlorin (Foscan), 5-aminolevulinic acid (Metvix) and Benzoporphyrin derivative, and/or nanotheranostics reagents.

The term "photosensitizers" relates to any substance able to induce photosensitivity in a subject. Photosensitivity is typically defined as a chemically induced alteration in the skin that makes a person more sensitive to light. Photosensitizers are for example molecules that rapidly destroy cells though the production of reactive oxygen species (ROS) when exposed to light at specific wavelength.

The term "photosensitivity" thus relates to the amount to which an object reacts upon receiving photons, especially visible light. Sensitivity of the skin to a light source can take various forms. Particular medications make the skin more sensitive to sunlight; these include most of the tetracycline antibiotics, heart drugs amiodarone, and sulfonamides. Examples for suitable photosensitizer according to the present disclosure are N-hydroxysuccinimide ester (IR700; also known as IRDye®700DX), porfimer sodium (Photofrin), meta-tetrahydroxyphenylchlorin (Foscan), 5-aminolevulinic acid (Metvix) and a fluorescent dye like Alexa-647. Alexa Fluor dyes are synthesized through sulfonation of coumarin, rhodamine, xanthene (such as fluorescein), and cyanine dyes. Alexa Fluor® 647 dye for example is a bright, far-red-fluorescent dye with excitation ideally suited for the 594 nm or 633 nm laser lines. For stable signal generation in imaging and flow cytometry, Alexa Fluor® 647 dye is pH-insensitive over a wide molar range. Alexa-647 is e.g. available from the Covalys Biosciences AG, Witterswil, Switzerland or Life Technologies Corporation. An example of the Alexa-647 chemical structure is:

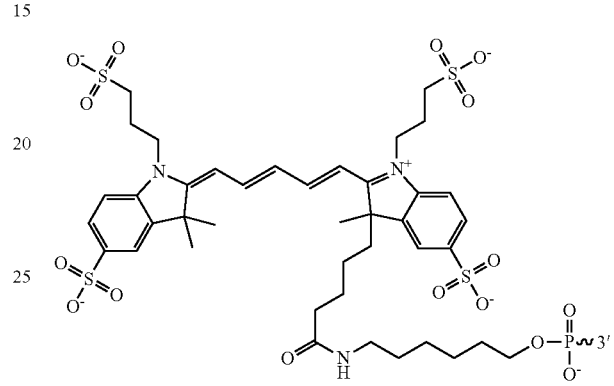

A "nanocarrier" is nanomaterial being used as a transport module for another substance, such as a drug. Commonly used nanocarriers include micelles, polymers, carbon-based materials, liposomes and other substances. The term "drug nanocarriers" can be primarily categorized into two main platforms. First, delivery of payload of a photo-reactive drug (e.g. a photosensitizer) using conventional nanoparticles, and second, design and development of photo-triggerable nanoparticles (primarily liposomes) to attain light-assisted on-demand drug delivery.

In another aspect the disclosure pertains to photoimmuno-theranostics reagent produced by the methods disclosed herein.

In one disclosure the photoimmuno-theranostics reagents disclosed herein are suitable for the use in detecting and/or diagnosing skin cancer in a patient and/or a tissue sample taken from a patient, e.g. during a biopsy.

In another disclosure the photoimmuno-theranostics reagents disclosed herein are suitable for the treatment of skin cancer in a patient and/or outside the body.

The term "patient" as used herein refers to both human subjects as well as animals in need of a detection, diagnosis or treatment of skin cancer.

Skin cancers are cancers that arise from the skin. They are due to the development of abnormal cells that have the ability to invade or spread to other parts of the body. There are three main types: basal cell cancer (BCC), squamous cell cancer (SCC) and melanoma. The first two together along with a number of less common skin cancers are known as non-melanoma skin cancer (NMSC). Basal cell cancer grows slowly and can damage the tissue around it but is unlikely to spread to distant areas or result in death. It often appears as a painless raised area of skin that may be shiny with small blood vessel running over it or may present as a raised area with an ulcer. Squamous cell cancer is more likely to spread. It usually presents as a hard lump with a scaly top but may also form an ulcer. Melanomas are the most aggressive. Signs include a mole that has changed in size, shape, colour, has irregular edges, has more than one colour, is itchy or bleeds.

Greater than 90% of cases are caused by exposure to ultraviolet radiation from the sun. This exposure increases the risk of all three main types of skin cancer. Exposure has increased partly due to a thinner ozone layer. Tanning beds are becoming another common source of ultraviolet radiation. For melanomas and basal cell cancers exposure during childhood is particularly harmful. For squamous cell cancers total exposure, irrespective of when it occurs, is more important. Between 20% and 30% of melanomas develop from moles. People with light skin are at higher risk as are those with poor immune function such as from medications or HIV/AIDS. Diagnosis is by biopsy.

Decreasing exposure to ultraviolet radiation and the use of sunscreen appears to be effective methods of preventing melanoma and squamous cell cancer. It is not clear if sunscreen affects the risk of basal cell cancer. Non-melanoma skin cancer is usually curable. Treatment is generally by surgical removal but may less commonly involve radiation therapy or topical medications such as fluorouracil. Treatment of melanoma may involve some combination of surgery, chemotherapy, radiation therapy, and targeted therapy. In those people whose disease has spread to other areas of their bodies, palliative care may be used to improve quality of life. Melanoma has one of the higher survival rates among cancers, with over 86% of people in the UK and more than 90% in the United States surviving more than 5 years.

Skin cancer is the most common form of cancer, globally accounting for at least 40% of cases. It is especially common among people with light skin. The most common type is non-melanoma skin cancer, which occurs in at least 2-3 million people per year. Of non-melanoma skin cancers, about 80% are basal cell cancers and 20% squamous cell cancers. Basal cell and squamous cell cancers rarely result in death. In the United States they were the cause of less than 0.1% of all cancer deaths. Globally in 2012 melanoma occurred in 232,000 people, and resulted in 55,000 deaths. Australia and New Zealand have the highest rates of melanoma in the world. The three main types of skin cancer have become more common in the last 20 to 40 years, especially in those areas which are mostly Caucasian.

The present disclosure also pertains to use of photoimmuno-theranostics reagent for detection, diagnosis or treatment of skin cancer.

The present disclosure also pertains to photoimmuno-theranostics reagents wherein the detection, diagnosis or treatment of skin cancer takes place outside the human body.

The present disclosure also pertains to photoimmuno-theranostics reagents wherein the detection, diagnosis or treatment of skin cancer takes place inside the human body.

The present disclosure also pertains to a kit comprising the disclosed photoimmuno-theranostics reagents for example for the use in skin cancer detection, diagnosis and/or treatment.

The present disclosure also pertains to pharmaceutical compositions comprising the disclosed photoimmuno-theranostics reagents.

The present disclosure also pertains to an anticancer drug comprising the photoimmuno-theranostics as an active ingredient thereof.

The present disclosure also pertains to a vector comprising a polynucleotide encoding a single-chain variable fragment antibody of SEQ ID No. 1.

The present disclosure also pertains to a host cell comprising above mentioned vector and/or producing a polynucleotide encoding a single-chain variable fragment antibody of SEQ ID No. 1.

The described photoimmuno-theranostics can then be used in photo-immunotherapy (PIT).

Photoimmunotherapy (PIT) is a new type of molecular targeted cancer therapy, which allows the selective destruction of cancer cells without any damage to normal tissues. It is a light-based cancer therapy, which was developed by Professor Kobayashi and his colleagues at National Cancer Institute, Bethesda, Md.

Conventional photodynamic therapy (PDT) uses a non-specific photosensitizer which can be activated by a non-ionizing light to kill cancer cells. Photosensitizers are molecules that rapidly destroy cells though the production of reactive oxygen species (ROS) when exposed to light at specific wavelength. However, this PDT treatment results in serious side effects because non-targeted photosensitizers are also taken up by normal tissues.

PIT treatment avoids the side effects problem through the creation of a targeted-photosensitizer, which involves two components: a monoclonal antibody (mAb) which recognizes specific proteins on the surface of cancer cells, and a non-targeted photosensitizer. Even though the new mAb-based photosensitizers are distributed throughout the body, it can be activated by light for targeted PIT only when bound to specific proteins on cancer cellular membrane.

The success of PIT therefore depends both on the appropriate selection of stable photosensitizer molecules as well as a moiety which binds selectively to the envisaged target.

Thus, one part of the present disclosure also pertains to suitable photosensitizer molecules which can be combined with the antibody fragment.

The phthalocyanine dye, N-hydroxysuccinimide ester (IR700; also known as IRDye®700DX) is activated by near-infrared light. Phthalocyanine was chosen because its hydrophilicity and strong cytotoxicity induced when associated with cellular membrane.

In Vitro studies showed that mAb-IR700 killed tumor cells seconds after the near-infrared light irradiation. There was also a positive correlation between the intensity of excitation light and percentage of cell death. Infrared light alone or mAb-IR700 conjugate alone did not cause any damage to normal cells. When tumor-xenografted mice were treated with mAb-IR700 and near-infrared light, significant tumor shrinkage was observed. With fractionated administration of mAB-IR700 conjugate followed by systematic repeated NIR light irradiation to the tumor, 80 percent of tumor cells war eradicated and the mice's survival were significantly prolonged. Based on the current hypothesis, cell death induced by PIT was caused by rapid expansion of local water upon the formation of holes in the membrane.

Thus, IR700 is disclosed in the examples as a suitable theranostic agent because of its high extinction coefficient and fluorescent quantum yield, which are 175-fold higher than those of Photofrin, 9-fold higher than those of meta-tetrahydroxyphenylchlorin Foscan and 5-fold higher than those of mono-L-aspartylchlorin e6 NPe6/Laserphyrin.

Another potential advantage of IR700 is the lack of passive diffusion properties. Therefore, cells do not take up IR700 and thus are not harmed after illumination. IR700 shows great photostability while producing a strong fluorescent signal. By fusing the SNAP-tag protein with an EFGR-specific scFv and conjugating it with BG-modified IR700 molecule is was possible to develop a stable photoimmuno-conjugate with 1:1 stoichiometry between fusion protein and label.

Therefore before PIT, mAb-IR700 can be administered at a lower dosage to guide the application of excitation light to tumor tissues, further minimizing unnecessary light exposure to surrounding tissues.

It was found that the photoimmuno-conjugate was able to bind specifically to three EGFR-expressing skin cancer cell lines followed by internalization, whereas no cellular fluorescence signal was detected after incubation of A2058 cell expressing low levels of EGFR or cells without EGFR expression.

Moreover, the phototoxic properties of scFv-425-SNAP-IR700 were investigated. The cellular viability and apoptosis assays results shown in FIGS. 5 and 6 confirm its ability to induce cell death selectively in EGFR$^+$ skin cancer cell lines. All three EGFR high target cell lines showed low viability after exposure to photoimmuno-conjugate and light, with EC50 values of 32 nM for A431, 45 nM for IGR-1 and 55 nM for IGR-39.

It is important to mention that the key difference between the technology disclosed herein and previous studies using IR700 is that the site-specific conjugation strategy disclosed herein is designed to produce photoimmuno-theranostic reagents with homogenized pharmacokinetic and bio-distribution properties of the antibody.

Furthermore, antibody fragments were used to generate the photoimmuno-theranostic reagents providing several advantages over monoclonal antibodies, including the simple introduction of site-specific conjugation sites, efficient solid tumor penetration, and rapid clearance by renal filtration.

In conclusion, the present disclosure provides a framework for using antibody fusion proteins with SNAP-tag that can be used both to monitor and treat different skin cancer cell lines in vivo and/or in vitro.

The following methods and examples are offered for illustrative purposes only, and are not intended to limit the scope of the present disclosure in any way.

Methods and Examples

1. Cell Lines

The human skin epidermoid carcinoma cell line A431 (ATCC: CRL-259), human embryonic kidney (HEK-293T) cell line (ATCC: CRL-11268) and the human melanoma cell line A2058 (ATCC: CRL-11147) were cultured in RPMI-1640 medium. The human melanoma cell line IGR-39 (DSMZ: ACC 239) and IGR-1 (DSMZ: ACC-236) were cultured in DEME medium. All media were supplemented with 2 mM L-glutamine, 10% (v/v) fetal bovine serum (FBS) and 100 U/mL penicillin-streptomycin; the cells were incubated at 37° C. in a 5% $CO_2$ atm. All media and additives were purchased from Life Technologies, Darmstadt, Germany.

2. Protein Expression and Purification

A mammalian cell expression system was used to express scFv-425-SNAP-tag fusion protein as described previously (9, 12). Briefly, 1 µg of pMS-scFv-425-SNAP-tag DNA was transfected into HEK-293T cells using RotiFect® (Carl Roth GmbH, Karlsruhe, Germany). Transfected cells were selected using 100 µg/mL zeocin and fluorescence activated cell sorting. Fusion protein was purified from cell-free supernatants via the C-terminal His-tag using Ni-NTA Superflow® cartridge (Qiagen, Hilden, Germany) on an ÄKTA® protein purification system (GE Healthcare Europe GmbH, Freiburg, Germany).

3. Modification of IR700 with Benzylguanine Group

IRDye®700DX N-hydroxysuccinimide ester (IR700) photosensitizer (LI-COR Biosciences GmbH, Bad Homburg, Germany) was modified with benzylguanine linkers (BG-NH$_2$ or BG-PEG$_{24}$-NH$_2$) (Covalys Biosciences AG, Witterswil, Switzerland) using the N-hydroxysuccinimide ester-amino group reaction as described by Hermanson 2008 (13). Briefly, benzylguanine linkers were incubated with IR700 overnight in the dark at room temperature in a 1:2 molar ratio. BG-modified IR700 molecules were analyzed and purified using a Prontosil® C-18 column (250×4.6 mm, 5 µm, 120 Å) (Bischoff Chromatography, Germany) on a high-performance liquid chromatography (HPLC) (Water, Eschborn Germany). Runs were monitored at 286 nm and 680 nm to visualize BG-linkers, IR700 and BG-modified IR700 molecules. The mobile phase flow rate was 1 mL/min. During the analytical and purification runs, gradient elution was carried out using mobile phases A [0.1M triethylammonium acetate (TEAA)] and B (0.1M TEAA and 70% acetonitrile). The BG-modified IR700 molecules were separated using a 55 min gradient of B from 0 to 100%.

4. Preparation of Photoimmuno-Theranostics Reagent

BG-modified IR700 molecules were conjugated to scFv-SNAP-tag fusion protein in a one-step reaction by mixing them individually with a 0.8-fold molar of fusion proteins for 2 h in the dark at room temperature. Even though the IR700 dye has many advantageous in vivo optical imaging properties, most of the traditional in vitro imaging devices (ex. flow cytometry and confocal microscopy) fail to detect its narrow NIR fluorescence peak. To overcome this limitation, the BG-Alexa-647 Dye® (Covalys Biosciences AG, Witterswil, Switzerland) has been conjugated to the fusion protein instead of BG-IR700 and used for flow cytometry and confocal microscopy analysis.

Labeled fusion proteins were cleaned up using Zeba Spin® Desalting Columns, 40K MWCO (Thermo Fisher Scientific, Rockford, Ill.). To further ensure the site-specific conjugation of BG-modified IR700 molecules, SNAP-tag fusion proteins were either blocked with bromothenylpteridine (BTP) (Covalys Biosciences AG, Witterswil, Switzerland) or post-incubated with BG-Vista Green® fluorescent dyes. We next determined the fluorescence signals of labeled proteins by visualizing them, after SDS-PAGE protein separation, using the CRi Maestro® imaging system (CRi, Woburn, Mass., USA). Furthermore, the theoretical extinction coefficient of the proteins and the extinction coefficients of the fluorescent dyes were used to estimate labeling efficiency photometrically.

5. Flow Cytometry Analysis

Flow cytometry analysis was performed to determine the binding properties of labeled scFv-SNAP-tag fusion protein against skin cancer cell lines. Approximately $4 \times 10^5$ cells each of the EGFR-positive skin cancer cell lines IGR-39, IGR-1 and A431 as well as of the EGFR low expressing cell line A2058 were incubated with 0.5 µg of labeled proteins for 30 min on ice. After washing the cells twice with 1.8 mL of PBS in a conventional cell washer, fluorescence signals were detected using a FACSCalibur® device and Cell-Quest® software (Becton & Dickinson, Heidelberg, Germany) using a 633 nm laser source.

6. Confocal Microscopy

To further monitor the targeted activity of fusion protein, Opera® High Content Screening System (PerkinElmer, Rodgau, Germany) was used to determine the binding and internalization properties of labeled fusion proteins on skin cancer cells. Cells were prepared as described for flow cytometry analysis. Binding activity was analyzed by incubating the cells with labeled fusion proteins for 30 min on ice, while receptor mediate internalization activities was monitored by incubating the cells with the labeled fusion proteins for 2 h at 37° C.

7. Phototoxicity of scFv-425-SNAP-IR700

In addition to the in vitro imaging specificity, the phototoxic activity of scFv-SNAP-IR700 and free IR700 were also investigated using cell proliferation and cell apoptosis assays as described previously (9). Briefly, $2 \times 10^4$ cells were seeded in 96-well plates and incubated overnight at 37° C. The cells were treated with different concentrations (0, 12.5, 25, 50, 100, 200 and 400) nM of scFv-425-SNAP, IR700 or equivalent concentration of scFv-SNAP-425-IR700 for 3 h at 37° C. in the dark. Toxic control cultures were incubated with 500 µg/mL zeocin instead of the photosensitizer.

Before light irradiation, cells were washed three times with PBS and fresh phenol red free culture media were added to the cells. Light treatment was performed with a Hydrosun® Typ 750 radiator with a water-containing cuvette and an orange filter OG590, with 140 mW/cm$^2$, dose: 25 J/cm$^2$a VIS, 76 J/cm$^2$ wIRA, exposure time: 15 min, and a spectrum in the range of 580-1400 nm (Hydrosun Medizintechnik GmbH, Mülhelm, Germany). During the light treatment, the temperature was controlled at 36° C. using a Multifunctional Double Block Cooling Thermostat (DITABIS, Pforzheim, Germany). After light treatment, cells were incubated in fresh medium as described before for 24 h. All light treatments were performed according to the physical and photobiological rules described by Piazena and Kelleher.

Cell viability was measured using the cell proliferation kit II (XTT®) (Roche, Mannheim Germany) according to the manufacturer's instructions. Briefly, XTT® labeling reagent was mixed with electron coupling reagent in 1:0.02 molar ratio. After that, 50 µL of XTT® labeling mixture were added to the cells and incubated for 4 h at 37° C. Cell viability was determined colorimetrically by monitoring the reduction of XTT® to formazan at 450 nm absorbance wavelength and 630 nm reference wavelength using the ELx808 absorbance micro-plate reader (BioTek Instruments GmbH, Bad Friedrichshall, Germany).

Next it was determined whether scFv-SNAP-IR700 has the ability to induce apoptosis using the Apo-ONE® Homogeneous Caspase-3/7 assay (Promega, Mannheim, Germany). After treating the cells as described above, the cells were incubated with Apo-ONE® reagent for 6 h at 37° C. The activities of caspase-3 and -7 enzymes were analyzed in cell lysates by measuring the fluorescence signal at 485 nm excitation wavelength and 535 nm emission wavelength using the ELISA plate reader ELx808 (Bio-TEK, Bad Friedrichschall, Germany).

8. Data Analysis

Statistical analysis and curve fitting were performed with GraphPad Prism® software (GraphPad software). Data represent the average of triplicates ±SEM. Student's t test and two-way analyses of variance were used to assess the significance of independent experiments, with $P<0.05$ as the threshold for statistical significance.

9. Synthesis of Benzylguanine-Modified IR700

In order to site specifically conjugate IR700 to scFv-SNAP-tag fusion protein, IR700N-hydroxysuccinimide ester molecules were modified with BG using either BG-NH$_2$ or BG-PEG$_{24}$-NH$_2$ linkers. The chemical coupling and purification of IR700 with BG linkers was successfully achieved and confirmed by HPLC analysis (FIG. 1).

10. Formation of Photoimmunoconjugates

Figure 2:
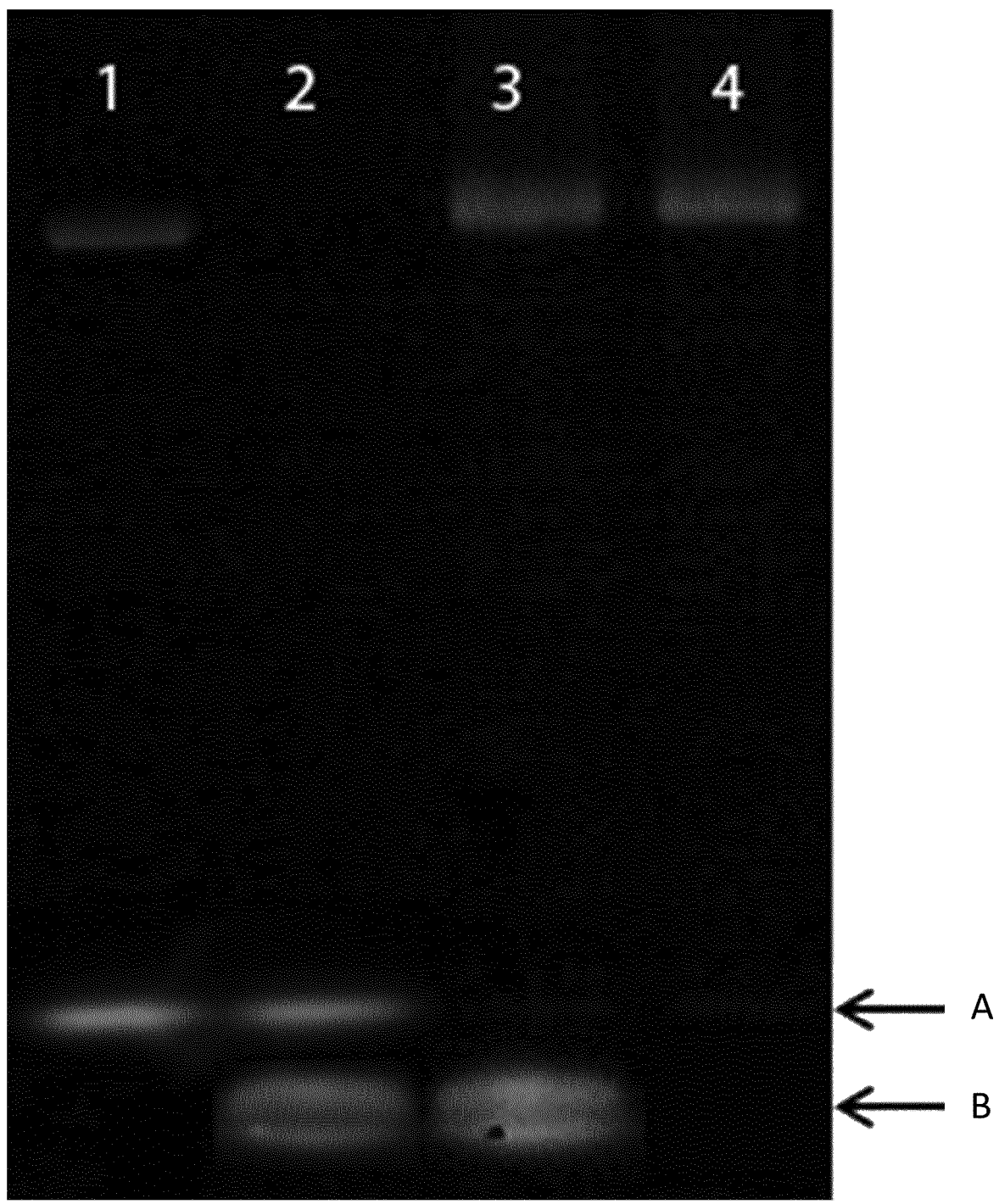
FIG. 2 shows the fusion protein labeling with BG-PEG$_{24}$-IR700. Fluorescence visualization of SDS-PAGE with BG-PEG$_{24}$-IR700 or BG-Vista Green coupled to scFv-425-SNAP-tag. Fusion protein was incubated with (1) 1.5-fold molar excess of BG-Vista Green; (2) bromothenylpteridine (BTP) SNAP-tag blocking reagent, and after that incubated with 1.5-fold molar excess of BG-PEG$_{24}$-IR700 for 2 h, then with 1.5-fold molar excess of BG-Vista Green; (3) 1.5-fold molar excess of BG-PEG$_{24}$-IR700; (4) and 1.5-fold molar excess of BG-PEG$_{24}$-IR700, followed by protein desalting. Vista Green and IR700 spectra were unmixed using CRi Maestro multispectral imaging system. Black arrows indicate free BG-Vista Green (Arrow "A") and BG-PEG$_{24}$-IR700 (Arrow "B").

The BG-647, BG-IR700 and BG-PEG$_{24}$-IR700 molecules were conjugated to an EGFR-specific scFv fused to the SNAP-tag. Unconjugated BG-PEG24-IR700 and BG-IR700 molecules were completely removed using Zeba Spin® Desalting Columns. Photometrical analysis revealed that approximately 85% of the fusion protein was labeled with BG-PEG$_{24}$-IR700 while BG-IR700 did not show any coupling to the scFv-425-SNAP-tag protein. Site-specific coupling activity of BG-modified molecules relies on irreversible transfer of the alkyl group to a cysteine residue in SNAP-tag. To confirm this reaction, we next explored conjugation properties of BG-modified IR700 molecules by incubating them with pre-blocked SNAP-tag fusion proteins; followed by incubation with BG-Vista Green® fluorescent dye. We found that BG-PEG$_{24}$-IR700 reacts solely with unblocked SNAP-tag protein, inhibiting the SNAP-tag and preventing its conjugation with the BG-Vista Green dye (FIG. 2). Unlike BG-PEG$_{24}$-IR700, BG-IR700 molecules were not able to conjugate with SNAP-tag proteins (data not shown).

11. Flow Cytometry and Confocal Microscopy

Figure 3:
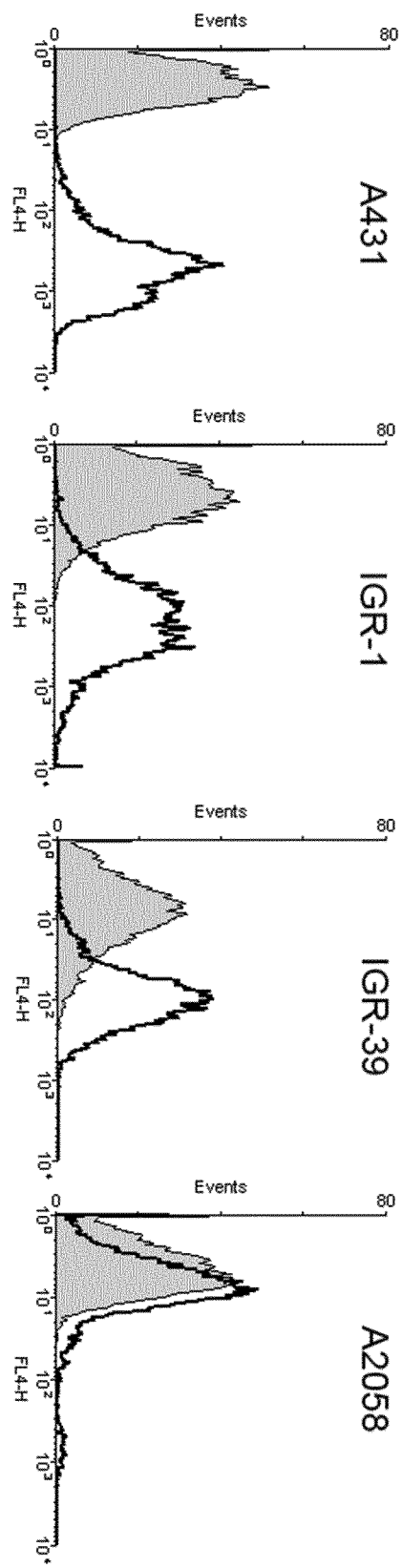
FIG. 3 shows a flow cytometry binding analysis of scFv-425-SNAP-647 against EGFR$^+$ skin carcinoma cell lines (A431, IGR1 and IGR-39) and EGFR low expressing A2058 cells. Filled gray curves represent untreated cells. Cells were incubated with 0.5 µg/ml scFv-425-SNAP-647 at 4° C. (black curve).
Figure 4:
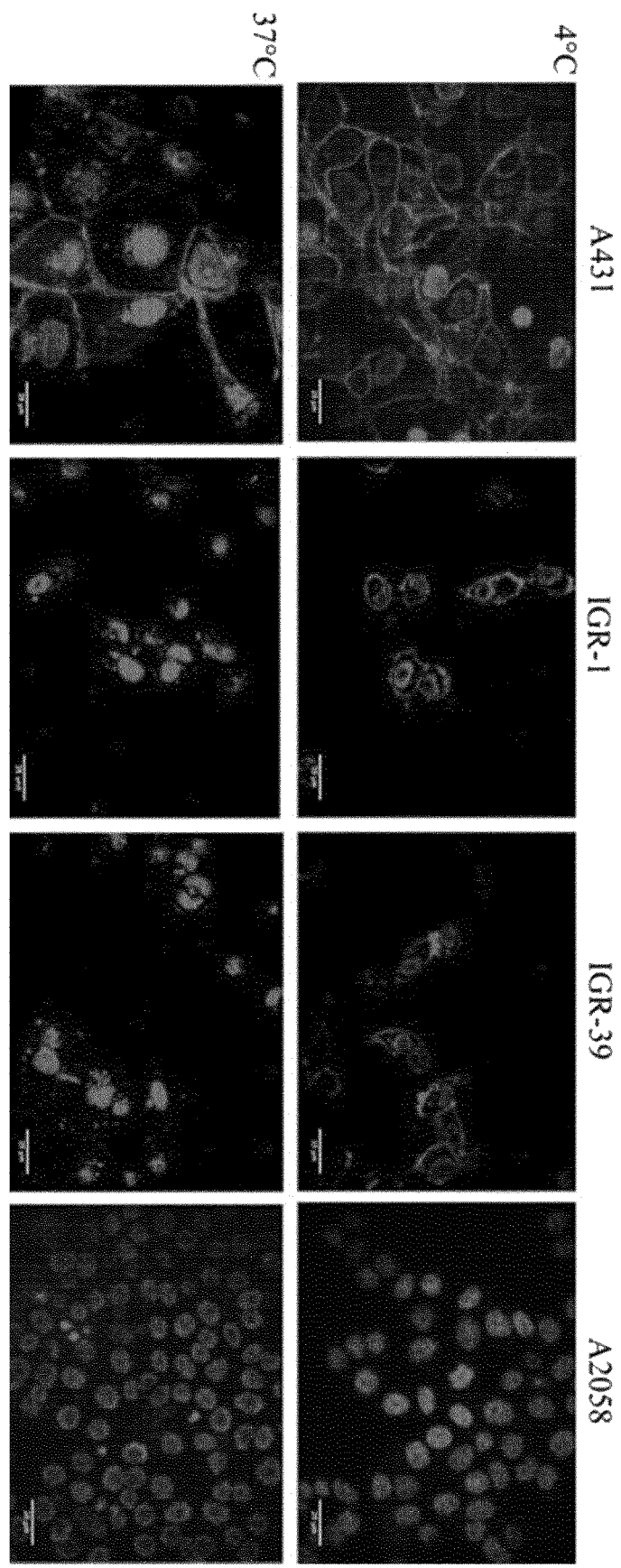
FIG. 4 shows confocal microscopy images of EGFR$^+$ skin carcinoma cell lines (A431, IGR1 and IGR-39) and EGFR low expressing A2058 cells exposed to scFv-425-SNAP-647 for 30 min at 4° C. (upper panel) or 2 h at 37° C. (lower panel).

The ability of photosensitizer-labeled scFv-425-SNAP-tag fusion protein to bind EGFR expressing skin cancer was investigated by flow cytometry. The results of this experiment confirm the rapid and efficient labeling of EGFR$^+$ skin cancer cells using scFv-425-SNAP-647, while minimal shift was observed on EGFR low expressing A2058 cell line under the same experimental condition (FIG. 3). To further confirm specific targeting of scFv-425-SNAP-647 to EGFR expressing cells, binding and internalization activity of the scFv-425-SNAP-647 were analyzed using confocal microscopy. All three EGFR-expressing cell lines showed homogeneous cell membrane staining after 30 min incubation at 4° C. Importantly, scFv-425-SNAP-647 was exclusively taken up into all EGFR$^+$ cell lines after max. 2 h of incubation at 37° C. In contrast, no signal was detected when the EGFR low expressing cell line (A2058) incubated with labeled fusion protein under the same conditions (FIG. 4).

12. Photoimmunotoxicity

Figure 5:
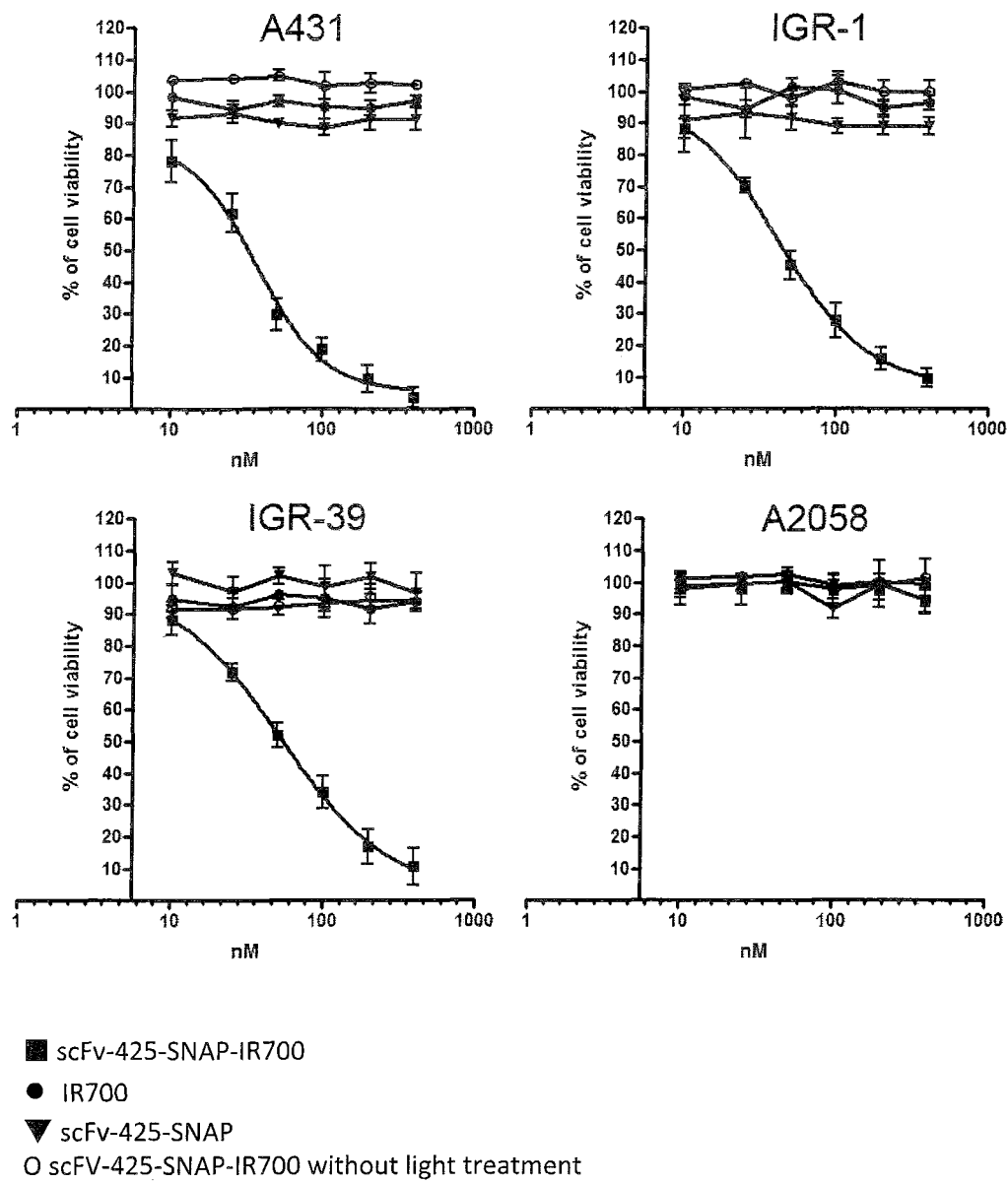
FIG. 5 shows a cell viability assay using scFv-425-SNAP-IR700. The cytotoxicity of scFv-425-SNAP-IR700, IR700, scFv-425-SNAP and scFv-425-SNAP-IR700 without light treatment against A431, IGR-1, IGR-39 and A2058. Cell viability was evaluated by carrying out an XTT assay using increasing concentrations of each reagent (0, 12.5, 25, 50, 100, 200 and 400 nM).

The photoimmunotoxic activities of scFv-425-SNAP-IR700 against the A431, IGR-1 and IGR-39 cell lines expressing high levels of EGFR and A2058 cells, which do express EGFR at low levels, were analyzed using a colorimetric cell viability assay (XTT kit). The viability of all EPFR$^+$ cells treated with scFv-425-SNAP-IR700 and light at a wavelength range of 580-1400 nm was reduced significantly in a concentration-dependent manner (FIG. 5). The EC$_{50}$ values were 32 nM for A431, 45 nM for IGR-1 and 55 nM for IGR-39 cells. In contrast, no significant reduction in cell viability was observed on A2058 cells treated with the same protocol. All the cells remained unaffected even when exposed to IR700 or unlabeled scFv-425-SNAP-tag protein and treated with NIR-light. Also, incubating cells with scFv-425-SNAP-IR700 without any light treatment yielded no toxic effects (FIG. 5).

Figure 6:
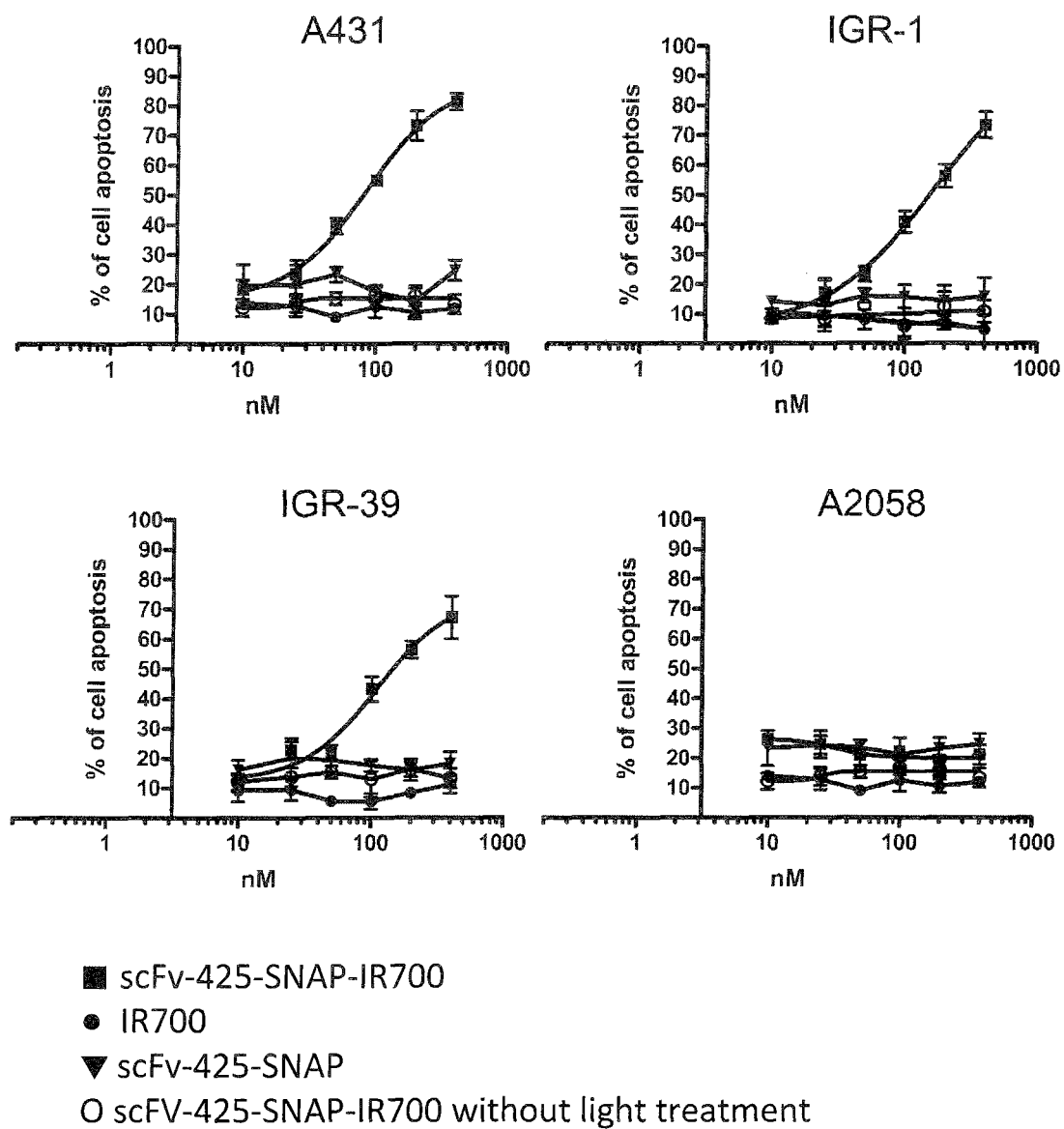
FIG. 6 shows a caspase-3/7 apoptosis assay. Induction of cell apoptosis was evaluated after exposing the cells to increasing concentrations (0, 12.5, 25, 50, 100, 200 and 400 nM) of scFv-425-SNAP-IR700, IR700, scFv-425-SNAP and scFv-425-SNAP-IR700 without light treatment.
Figure 7:
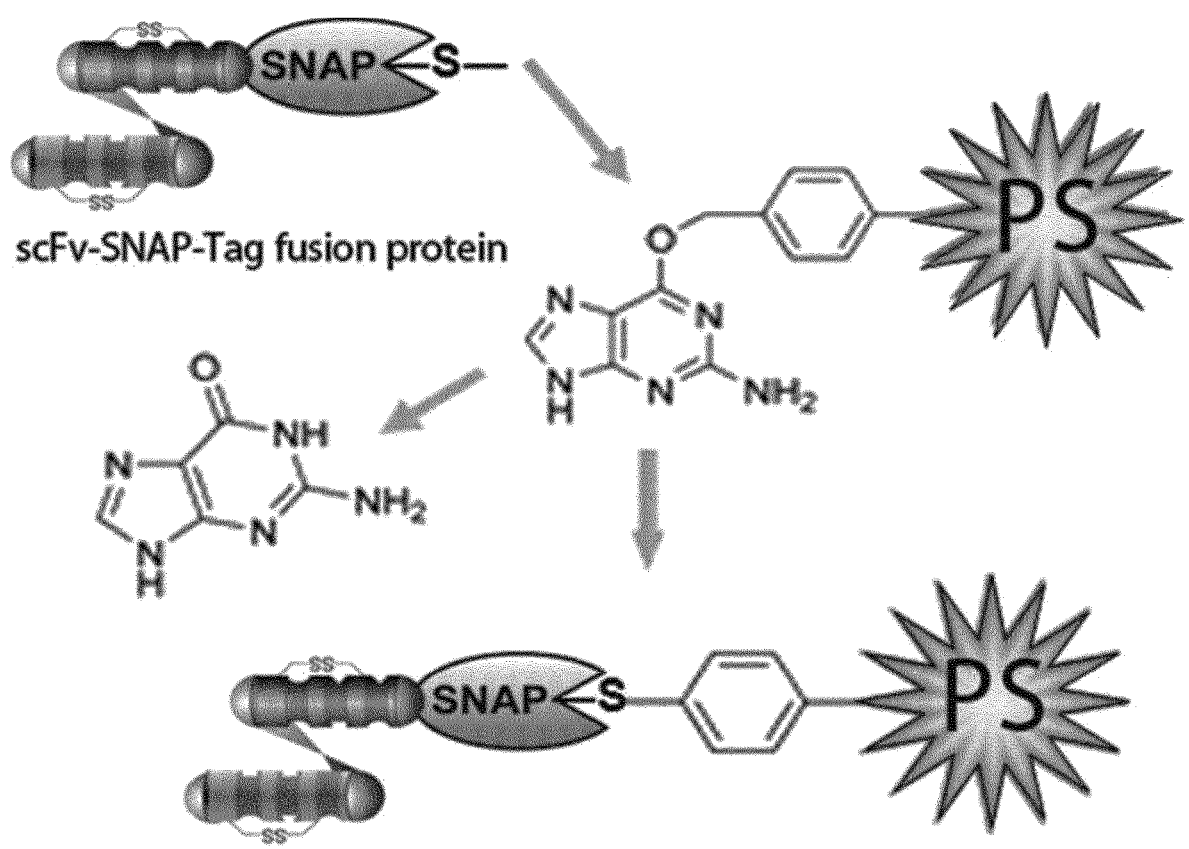
FIG. 7 shows a schematic depiction of the one step covalent binding reaction of the antibody-fragment-SNAP-tag-fusion protein with BG-modified molecules, e.g. "photosensitizers" (PS).

To investigate whether scFv-425-SNAP-IR700 was inducing selective cell death by apoptosis, we determined caspase-3 and caspase-7 activities in the treated cells using the Apo-ONE® Caspase-3/7 assay. We found that scFv-425-SNAP-IR700 triggers apoptosis of all cells expressing EGFR in a dose dependent manner, whereas scFv-425-SNAP-IR700 did not have a negative impact on EGFR low expressing cells (A2058) treated under the same conditions. Furthermore, no significant elevation of caspase activities was detected after incubating of cells with the photosensitizer or fusion protein alone (FIG. 6).

REFERENCES

The contents of all cited references, including literature references, issued patents, and published patent applications, as cited throughout this application are hereby expressly incorporated by reference.

Antibodies: A Laboratory Manual, (Cold spring Harbor Labaratory Press, 4th ed. (2014), by Hammerling, et al.

Huston et al., Methods in Enzymology 203:46-88 (1991)

Shu et al., PNAS 90:7995-7999 (1993)

Skerra et al., Science 240:1038-1040 (1988).

---

What is claimed is:

1. A photoimmuno-theranostic reagent comprising an scFv-425-SNAP-tag fusion protein conjugated to N-hydroxysuccinimide ester (IR700) through a benzylguanine (BG) linker, wherein the scFv-425 is a single chain variable fragment antibody having the amino acid sequence of SEQ ID NO. 1;

wherein the SNAP-tag has the amino acid sequence of SEQ ID NO. 2; and wherein the N-hydroxysuccinimide ester (IR700) has the formula:

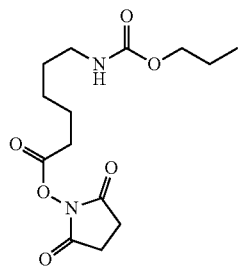

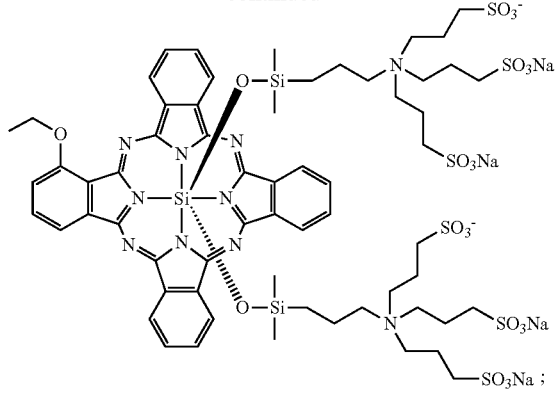

wherein the BG linker is BG-PEG$_{24}$-NH$_2$; and wherein the BG linker attaches to the N-hydroxysuccinimide ester (IR700) via a N-hydroxysuccinimide ester-amino group reaction.

2. A method of diagnosing and/or treating skin cancer comprising administering to a patient in need thereof the photoimmuno-theranostic reagent of claim 1.

3. The method of claim 2, wherein the skin cancer to be diagnosed and/or treated is selected from the group consisting of basal cell cancer (BCC), squamous cell cancer (SCC), and melanoma.

4. The method of claim 2, wherein cells of the cancer diagnosed and/or treated express epidermal growth factor receptor (EGFR).

5. An anticancer drug comprising the photoimmuno-theranostic reagent according to claim 1, as an active ingredient thereof.

* * * * *